United States Patent
Hipp et al.

(10) Patent No.: US 6,440,150 B1
(45) Date of Patent: Aug. 27, 2002

(54) MEDICAL SCISSORS WITH WEAR-REDUCING COATING

(75) Inventors: Gottfried Hipp, Carl-Benz-Strasse 1, D-78579 Neuhausen; Bernhard Schröder, Lichtenstein; Michael Sellschopp, Tübingen; Günter Durst, Kohlberg, all of (DE)

(73) Assignee: Gottfried Hipp, Neuhausen (DE)

( * ) Notice: Subject to any disclaimer, the term of this patent is extended or adjusted under 35 U.S.C. 154(b) by 0 days.

(21) Appl. No.: 09/336,517

(22) Filed: Jun. 18, 1999

Related U.S. Application Data

(63) Continuation of application No. PCT/EP97/07093, filed on Dec. 17, 1997.

(30) Foreign Application Priority Data

Dec. 21, 1996 (DE) .......................... 196 52 821

(51) Int. Cl.$^7$ .............................................. A61B 17/00
(52) U.S. Cl. ...................................... 606/174; 427/2.1
(58) Field of Search .......................... 606/1, 174, 167, 606/205–210; 30/173, 194, 224; 428/457, 447; 427/2.1, 2.28, 452, 556

(56) References Cited

U.S. PATENT DOCUMENTS

| | | | |
|---|---|---|---|
| 3,802,078 A | * | 4/1974 | Denes .................. 204/192.16 |
| 4,357,382 A | | 11/1982 | Lambert et al. |
| 5,152,774 A | * | 10/1992 | Schroeder .................. 606/174 |
| 5,507,760 A | | 4/1996 | Wynne et al. |
| 5,584,845 A | * | 12/1996 | Hart .......................... 606/174 |
| 5,613,977 A | | 3/1997 | Weber et al. |
| 5,795,648 A | * | 8/1998 | Goel et al. ................ 30/346.53 |
| 5,827,281 A | * | 10/1998 | Levin ......................... 606/174 |

FOREIGN PATENT DOCUMENTS

| | | |
|---|---|---|
| DE | 4235023 A1 | 1/1994 |
| DE | 4212053 C | 1/1996 |
| DE | 19652821 C1 | 4/1998 |
| EP | 0191203 A2 | 8/1986 |
| EP | 0194652 A1 | 9/1986 |

* cited by examiner

*Primary Examiner*—Michael J. Milano
*Assistant Examiner*—Vy C. Bui
(74) *Attorney, Agent, or Firm*—Harness, Dickey & Pierce, P.L.C.

(57) ABSTRACT

Medical scissors have handle parts and blades and are characterized in that they are coated, at least in the area of the blades, with an amorphous thin layer containing silicon, carbon and hydrogen, where the proportion of silicon is up to 100% atom parts in the boundary layer to the metallic body of the scissors, and up to 30% atom parts in the area of the outer surface of the layer.

13 Claims, 2 Drawing Sheets

MEDICAL SCISSORS WITH WEAR-REDUCING COATING

CROSSREFERENCE OF PENDING APPLICATION

This application is a continuation of pending international application PCT/EP 97/07093 filed on Dec. 17, 1997.

BACKGROUND OF THE INVENTION

1. Field of the Invention

The present invention relates to medical scissors having handle parts and blades.

Medical scissors normally consist of high-alloy stainless steel (medical steel). The scissors are hardened and polished so as to guarantee good cutting properties over an extended period of time.

Good cutting properties require, however, a specific contact pressure between the halves of the scissors. During the cutting operation as such, the blades move about a substantially point-shaped pivot area relative one to the other. This means that the cutting force is concentrated substantially at the substantially point-shaped crossing area of the two blades that move relative one to the other.

Due to the relatively high friction factor of the steel grades usually employed, a certain tightness, with corresponding wear, of the halves of the scissors, predominantly in the blade area, cannot be avoided. The sharp condition of the medical scissors is therefore limited, and the scissors loose their optimum cutting behavior rapidly.

Especially high demands are placed on the material of medical scissors because these are regularly sterilized with super-heated water vapor at high temperatures. The scissors therefore have to be corrosion-resistant.

In addition, the scissors must exhibit a high degree of biological inertness, as even slightest traces of abrasion of the blades may trigger allergic reactions with sensitive persons.

In addition, the cut as such should be as clean as possible, i.e. it should be applied atraumatically.

Even a slight contusion of tissue leads to increased bleeding when separating tissue parts in live bodies.

Increased bleeding delays the healing process, whereas clean edges of a wound will unite more rapidly.

2. Related Prior Art

DE 42 35 023 A1 describes a gripping and/or cutting instrument for endoscopic purposes, that can be guided precisely and permits extremely clean cuts to be made without the surrounding tissue being damaged. It is proposed for this purpose to provide certain components with a friction-reducing material, such as polytetrafluoroethylene.

From DE 42 12 053 C1 a surgical instrument, made from metal, has been known for thermally cutting and/or coagulating biological tissue, where the metallic surface is coated, at least in part, with a hard substance. The hard substance coating consists of one metal-metalloid compound, or a mixture of metal-metalloid compounds, where the metal is one from the fourth to eighth side-groups or an element of the third main group of the periodic system of the elements, and where the metalloid is selected from the group containing nitrogen, carbon, oxygen and boron. The hard substance layer may consist of (TiNb)ON, containing 41 atom percent of titanium, 19 atom percent of niobium, 31 atom percent of nitrogen and 9 atom percent of hydrogen. The precious-metal layer may have a thickness of between 0.01 and 3 micrometers.

Prom U.S. Pat. No. 5,507,760 a cutting tool for introduction into a catheter has been known, having a base that may be made from steel selected from the group of the 440 FSe and 440 C steels. The cutting edge exhibits a low-friction and hardening layer selected from diamond-like carbon, aluminium oxide, titanium nitride, titanium carbonitride, zircon nitride, boron nitride, cubic boron nitride and high-chromium compounds.

U.S. Pat. No. 5,152,774 describes medical scissors where a base of stainless steel or titanium is coated with a nitride layer by means of a VD process. The nitride layer is selected from the group consisting of titanium nitride, titanium nitride alloys and zirconium nitride, that are deposited at temperatures of 175 to 225° Celsius. The nitrided portion of the instrument has a Rockwell hardness "C" of at least approximately 50.

In the case of the known scissors mentioned above, the requirements previously mentioned are not fulfilled satisfactorily.

Thus, it is the object of the present invention to improve scissors of the before-mentioned kind in such a way that they will move easily, i.e. cut with little friction, that they will cut atraumatically, i.e. produce clean, rapidly healing cuts, and that are biologically inert and corrosion-proof.

SUMMARY OF THE INVENTION

This object is achieved according to the invention by the fact that the scissors are coated, at least in the area of the cutting edges, with an amorphous thin layer containing silicon, carbon and hydrogen, where the proportion of silicon is up to 100% atom parts in the boundary layer to the metallic body of the scissors, and up to 30% atom parts in the area of the outer surface of the layer.

With this configuration and a gradient in the silicon content and in the carbon and hydrogen as the other components, respectively, it is possible to achieve a coating which is extremely smooth and very hard and, in addition, chemically and biologically inert.

The very smooth layer is achieved by the fact that the layer is precipitated as amorphous layer. A crystalline layer would be considerably rougher due to the formation of crystallites.

The amorphous smooth layer allows low-friction and easy cutting, and the hardness of the layer produces in addition a wear-reducing effect.

Thus, it is possible with scissors coated in this way to make atraumatic cuts, and this permanently, as will appear from the test to be described later, where 10,000 cuts were made with a pair of scissors according to the invention without any variation, whereas in the case of conventional scissors increasing abrasion could be observed already after 500 cuts.

Due to the gradient in the silicon content according to which the latter is very high at the boundary surface to the base of the scissors, it is possible to achieve excellent binding of the layer to the base of the scissors. The declining silicon content and the resulting increasing content of carbon and/or hydrogen in the layer near its outer surface leads to an extremely hard, smooth and amorphous structure that presents the properties sought. The amorphous layer, consisting of silicon, carbon and hydrogen, is chemically and biologically inert, which means that there is no risk of corrosion of the layer, neither by chemical substances nor by biological attacks, if any.

The extreme hardness and smoothness of the outer surface of the layer can be explained by the fact that while $sp^3$ hybrid structures, i.e. the basis for a diamond-like lattice, are present in the carbon and the silicon as well, the formation of crystals is obviously prevented by the hydrogen as "interfering substance".

The object of the invention is thus perfectly achieved.

The content of silicon at the boundary layer amounts preferably to up to 95% atom parts, most preferably to 10 to 90% atom parts.

The term "percent atom parts" is used to describe the number of specific atoms, related to the total of 100 atoms.

It is further preferred that the content of silicon in the area of the surface amounts to 0 to 30% atom parts, and that at the same time the content of hydrogen in the layer amounts to 10 to 50% atom parts, the rest being carbon.

Within this variation range, it is possible on the one hand to achieve very good binding of the layer to the metallic base of the scissors and, on the other hand, to produce an extremely smooth, amorphous and hard layer on the outside, due to the higher carbon content. In both areas usual coating methods can be used by which the three components silicon, carbon and hydrogen can be precipitated in varying proportions.

Preferable, the thickness of the layer is 0.5 to 5 μm, or most preferably 0.5 to 2 μm.

These low thicknesses of the layer already permit to achieve excellent results so that medical scissors can be coated according to the invention with an economically reasonable input of material and equipment.

Most preferably, the layer consisting of silicon, carbon and hydrogen is precipitated by the PVD process (physical vapor deposition) and/or the CVD process (chemical vapor deposition), especially by the PECVD process (plasma-enhanced chemical vapor deposition).

By using these precipitation methods it is possible in an easy way to produce the desired layer with the desired gradient in silicon content.

If, for example, it is desired to apply exclusively silicon at the boundary surface to the base of the scissors, this can be effected by means of a PVD process, for example by what is known as sputtering. Small hydrogen contents can be realized by precipitating amorphous Si:H by a PECVD process, which makes use for example of silicon/hydrogen compounds. The subsequent deposits with a content of carbon can be produced especially by PECVD methods using compounds containing silicon, carbon and hydrogen, for example silicon/methyl compounds. The higher proportion of carbon may be achieved by introducing gradually into a PECVD process compounds richer in carbon, such a hydrocarbons, so that the layer can be built up with the desired gradient in a defined way and with smooth transitions.

Particular preference is given to a PECVD process where initially the halves of the scissors are cleaned from a possible oxide layer in an inert gas plasma, whereafter the corresponding gases are added for applying the inventive layer of silicon, carbon and hydrogen on the now extremely fine base of the scissors.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

Further advantages are evident from the exemplary embodiments below and in conjunction with the drawings, in which.

DETAILED DESCRIPTION OF PREFERRED EMBODIMENTS

Figure 1:
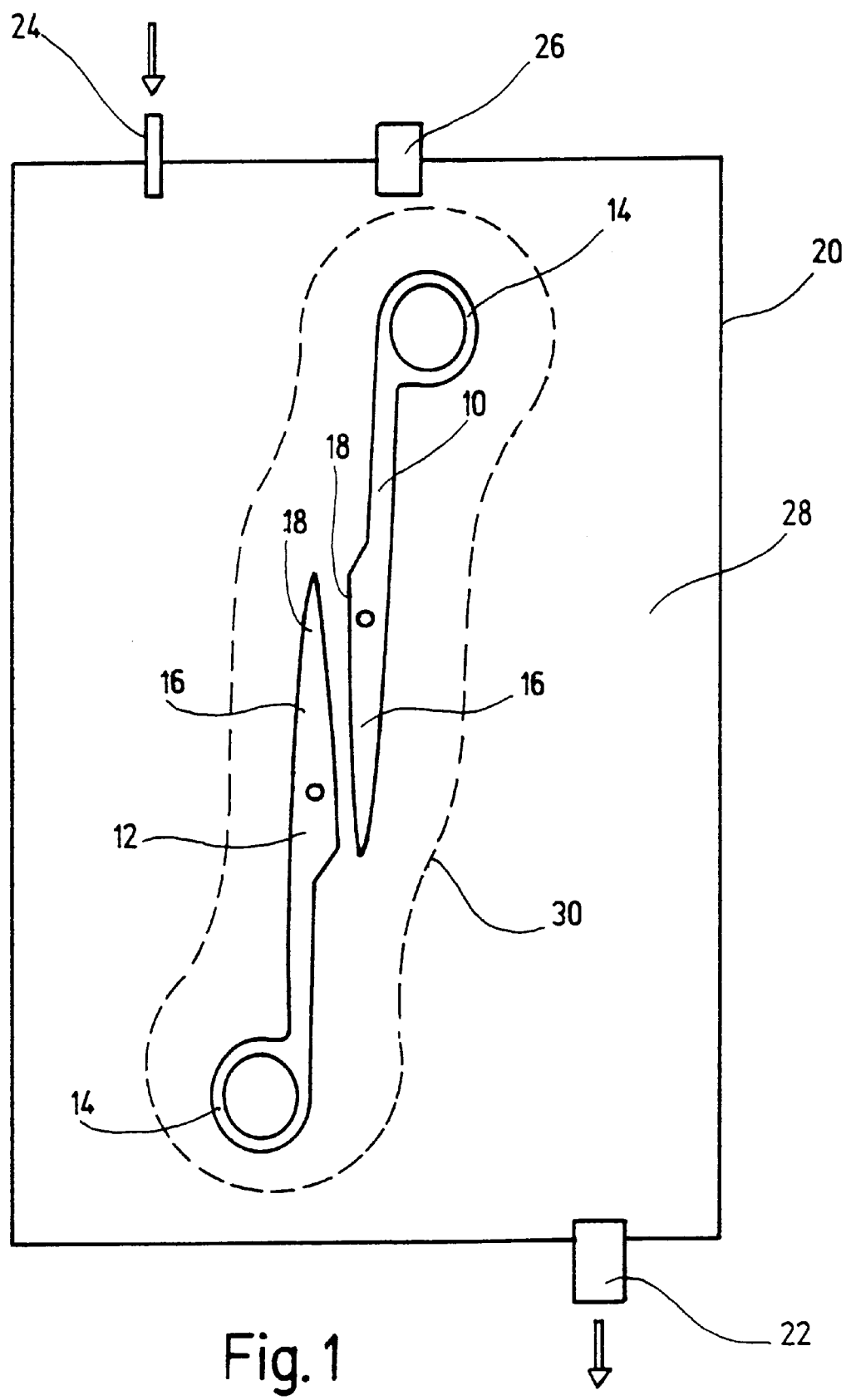
FIG. 1 shows a very diagrammatic representation of a device for carrying out the coating method according to the invention.

A pair of medical scissors according to the embodiment illustrated in FIG. 1 consists of two halves 10 and 12.

Each half comprises a handle portion 14, a blade portion 16 and a cutting edge 18.

The metallic base 19, which consists of a forging blank (see FIG. 2), is formed to a blank by drilling, milling and polishing.

The blank of the scissors is then dressed by hand, i.e. the two halves 10 and 12 are exactly adapted one to the other. The scissors so dressed are then hardened (hardness≧50 HRC, hardness after Rockwell, process C).

The dressed and hardened scissors are surface-treated (for example by grinding, polishing, vibratory grinding) in order to give them a superior surface quality to make them corrosion-proof.

The halves 10, 12 receive a particularly high surface quality especially in the area of the cutting edges 18.

For purposes of the coating process the halves 10 and 12 are initially degreased, for example by washing them in acetone, whereafter they are subjected to an alkaline and acid fine-cleaning process, and finally rinsed with deionized water, and dried.

The cleaned halves 10 and 12 are mounted in a special holder (not shown in the drawing) in such a way that their polished sides point to the outside. The holder, with the halves 10 and 12 mounted therein, is introduced into a vacuum chamber 20 of a PECVD system, and the latter is evacuated to a pressure of below $10^{-5}$ mbar. To this end, a suction opening 22 is provided in the vacuum chamber 20 and connected with corresponding vacuum pumps.

Thereafter, a flow or argon is introduced into the vacuum chamber 20 until a pressure of between $5 \times 10^{-2}$ and $5 \times 10^{-1}$ mbar is reached, and a high frequency of 13.56 MHz is supplied to the halves 10, 12 to cause a plasma to ignite.

The vacuum chamber 20 is provided for this purpose with a gas inlet opening 24 and a high-frequency supply line 26. Consequently, a plasma 28 forms inside the vacuum chamber 20, the halves 10 and 12 being surrounded by the so-called dark space 30 of the plasma 28. The high-frequency power is adjusted in such a way as to cause a direct voltage potential of −100 to −600 Volts, preferably −500 Volts, to build up on the scissors.

The plasma 28 acts to remove an oxide layer from the surface of the halves 10 and 12 in approximately 10 minutes.

Without shutting off the plasma 28, one introduces into the chamber 20, through the inlet opening 24, a gas containing silicon, carbon and hydrogen, for example TMS (tetramethylsilane) instead of the argon, whereby a layer of silicon, carbon and hydrogen builds up on the boundary layer to the base of the scissors. The layer depositing at the beginning has a very high content of silicon, namely approximately 30% atom parts, and a high carbon content of approximately 50%.

After a few minutes, acetylene is introduced into the vacuum chamber 20 as an additional gas, while simultaneously the TMS content is reduced, so that at the end of the coating process the silicon content of the layer is approximately 5% atom parts on the outer surface of the layer, the rest being approximately 30% atom parts of hydrogen and approximately 65% carbon.

Figure 2:
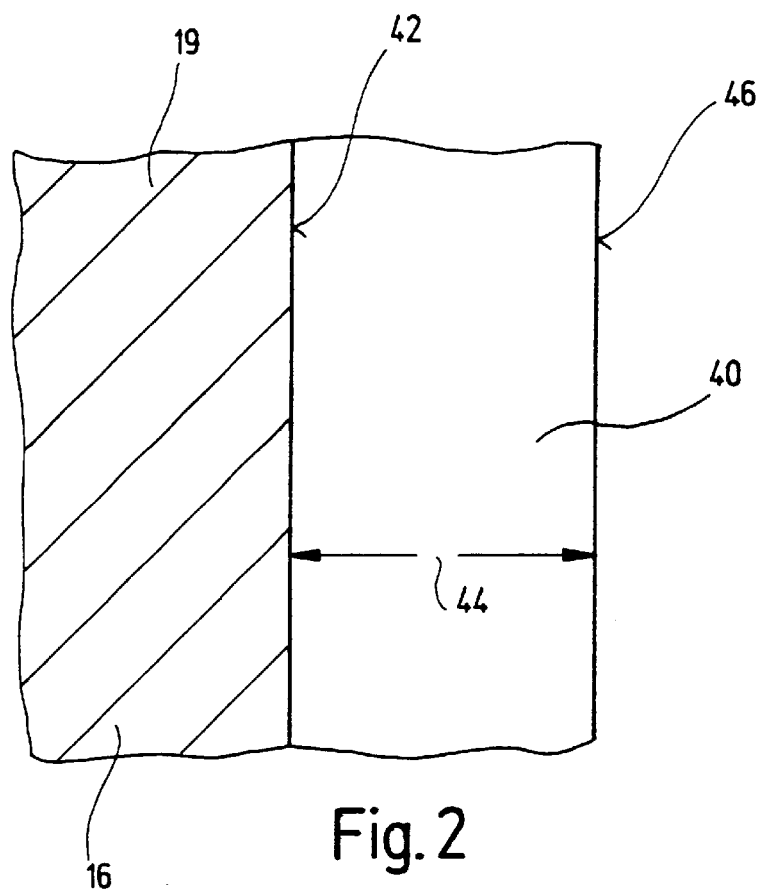
FIG. 2 shows a cross-section through a pair of scissors, in the area of its cutting edge, after coating according to the invention.

FIG. 2 shows a greatly enlarged cross-section through a detail of one half of the scissors in the blade area 16, as obtained after the coating treatment described above.

As will be noted, a layer 40 has been applied on the metallic base 19. The layer 40 has a thickness 44 of approximately 3 μm.

Figure 3:
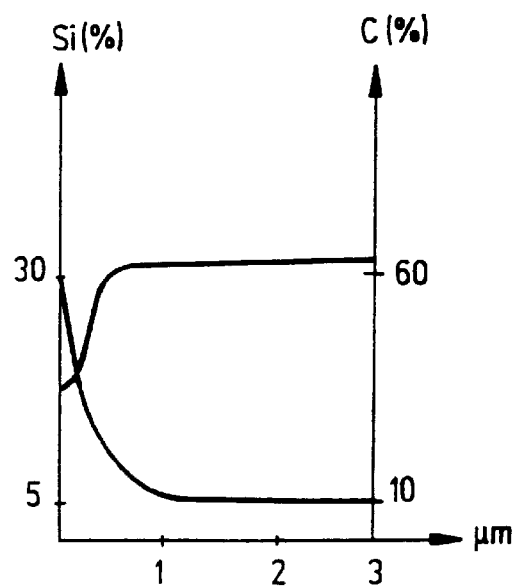
FIG. 3 shows a diagram of the structure of the layer according to FIG. 2.

In FIG. 3, the varying structure of the layer 40 is illustrated in the form of a diagram as a function of the thickness 44.

It can be seen that starting out from a boundary surface 42 between the metallic base 19 and the layer 40 a layer with a relatively high silicon content (approximately 30%) and a carbon content of approximately 50% has precipitated by the final coating step with tetramethylsilane. By adding acetylene as an additional gas, the carbon content rises and the content of silicon decreases, in relative terms. In the area of the outer surface 46 the silicon content is approximately 5% atom parts, the carbon content approximately 65% atom parts.

With respect to the degree of coverage of the cutting edges in the PECVD process it has been found to be advantageous to arrange the cutting edges 18 of the halves 10, 12 at a distance of 1 to 10, preferably 2 to 5 mm. In addition, it has been found to be advantageous to apply a bias of −100 to −600 Volts, preferably −200 to −400 Volts, on the halves of the scissors during the coating process.

The pressure in the vacuum chamber is maintained at approximately $2 \times 10^{-2}$ to $2 \times 10^{-1}$ mbar.

According to further embodiments of the invention, a monosilane is used instead of TMS, whereby a higher silicon content of up to 90% atom parts is obtained at the boundary surface 42 between the scissors and the layer 40 to be built up.

It is also possible to replace the PECVD process step for producing the silicon-rich boundary layer initially by a sputtering process, i.e. one where silicon is exclusively applied by sputtering from a target, after plasma cleaning of the halves 10 and 12. In this case, advantageously a silicon-containing carbon layer is applied immediately thereafter on the silicon produced by sputtering, by means of a PECVD process with the aid of silicon and carbon-containing gases.

This method of proceeding allows to have at first only silicon deposited at the boundary surface, and to then gradually increase the hydrogen content of the deposited layer by adding ethylene to the gas.

From the above examples it appears that the transitions between the varying proportions of the individual components silicon, carbon and hydrogen in the layer can be made very smooth, which means that it is thus possible to form a layer that adheres firmly not only to the base, but also to itself and that is extremely hard and smooth on the outside.

Investigations have shown that carbon molecules are present in XPS (X-ray induced photoelectron spectroscopy) and in the TEM (Transmission electron microscope) as $sp^3$ hybrid and thus have diamond-like structure elements, without any crystallites being formed that would have a detrimental effect on the smoothness.

Other process designs are also possible, for example to use magnetic fields to increase the degree of ionization of the plasma.

Further, it is also possible to precipitate silicon and carbon-containing layers with the aid of lasers or arc vaporization, all these procedures being covered by the present invention.

Test of the Corrosion-protection Properties

A pair of stainless-steel scissors, i.e. a pair of scissors made from special stainless steel for scissors, was taken apart, one half was coated according to the invention, the other remained uncoated.

The surfaces of the two halves were covered with a shrink-on hose in the area of the threaded bores over an area of 1 to 2 cm.

Both halves were subjected to the action of a solution containing 2.5% acetic acid and 1% NaCl (sodium chloride), at the following temperature cycle:

4 hours and 40 minutes at 80° Celsius, cooling down for 10 minutes to −10° Celsius, holding 1 hour at −10° Celsius, heating up for 10 minutes to 80° Celsius. This cycle was repeated four times.

Results

The standard stainless-steel half of the scissors showed a clearly visible grain structure on the uncovered surface, which is clearly due to corrosion effects caused by the treatment. The solution exhibited a slightly red color, which indicates that chromium has been removed. The covered part of the surface of the standard stainless-steel half was bright as before.

That half of the scissors that had been coated in accordance with the invention did not show any optically visible changes on the uncovered area of the surface. The solution was clear. The visual impression of the covered surface (after the film had been removed) corresponded optically to the free surface that had been exposed to the corroding agent.

Test of the Cutting Properties

A pair of standard stainless-steel scissors and a pair of scissors that had been coated in accordance with the invention were driven by an eccentric to simulate cutting movements.

Results

| Cutting cycles | Standard stainless-steel scissors | Scissors coated according to the invention |
|---|---|---|
| 200 | first signs of abrasion | no change |
| 500 | increasing signs of abrasion | no change |
| 1000 | further increasing signs of abrasion | no change |
| 2000 | abrasion gets so heavy that cutting edges become blunt; interruption of test | no change |
| 10000 | | no change |

The above results show the long service lives that can be achieved with scissors coated according to the invention.

What is claimed is:

1. A medical scissors of a pair of scissors halves, each of said halves having a cutting edge, wherein said scissors are coated, at least in an area of said cutting edges with an amorphous thin layer containing silicon, carbon and hydrogen, and wherein a decreasing content of silicon is present in a direction from a boundary layer to a metallic body of said scissors to the outer surface of said layer.

2. The medical scissors of claim 1, wherein the content of silicon in said boundary layer is approximately 10 to 100% atom parts.

3. The medical scissors of claim 2, wherein the content of silicon at the outer surface of said layer is up to 30% atom parts.

4. A method for producing medical scissors having a pair of scissors halves, each of said halves having a cutting edge characterized by precision-working of a metallic base of said scissors, coating said metallic base, at least in an area of said cutting edges with a thin amorphous layer containing silicon, carbon and hydrogen in such a way that a content of silicon at a boundary surface to said metallic base is approximately 10 to 100% atom parts and a silicon content in an area of an outer surface of said layer is up to 30% atom parts silicon.

5. The method of claim 4, wherein prior to said coating, a cleaning step is performed in an argon plasma.

6. The method of claim 4, wherein said coating is effected by means of a PECVD process.

7. The method of claim 6, wherein said PECVD process is carried out by means of a high-frequency charge, preferably with 13.56 MHz at a pressure of $2 \times 10^{-2}$ to $2 \times 10^{-1}$ mbar.

8. The method of claim 7, wherein said halves of said scissors are arranged during said PECVD process in such a way that said cutting edges are placed in one plane at distances of 1 to 10 mm.

9. The method of claim 8, wherein said cutting edges are placed at distances of 1 to 5 mm.

10. The method of claim 9, wherein said PECVD process is carried out using tetramethylsilane and acetylene.

11. The method of claim 10, wherein a bias of −100 to −600 Volts is supplied to said halves of said scissors during coating.

12. The method of claim 11, wherein said bias during said coating is in the range of −200 Volt to −400 Volt.

13. The method of claim 4, wherein said coating is effected by means of a PVD process in combination with a PECVD process.

\* \* \* \* \*